(12) United States Patent
Bakac et al.

(10) Patent No.: US 8,507,730 B1
(45) Date of Patent: Aug. 13, 2013

(54) SELECTIVE OXIDATION OF ORGANIC SUBSTRATES TO PARTIALLY OXIDIZED PRODUCTS

(75) Inventors: Andreja Bakac, Ames, IA (US); Oleg Pestovsky, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 13/434,900

(22) Filed: Mar. 30, 2012

Related U.S. Application Data

(60) Provisional application No. 61/473,316, filed on Apr. 8, 2011.

(51) Int. Cl.
*C07C 45/27* (2006.01)
*C07C 45/40* (2006.01)

(52) U.S. Cl.
USPC .......................................... 568/430; 568/469

(58) Field of Classification Search
USPC .................................................. 568/430, 469
See application file for complete search history.

(56) References Cited

U.S. PATENT DOCUMENTS

| | | |
|---|---|---|
| 4,008,286 A | 2/1977 | Hirose et al. |
| 6,576,144 B1 | 6/2003 | Vineyard |
| 7,618,546 B1 | 11/2009 | Bakac et al. |
| 2004/0217326 A1 | 11/2004 | Souter et al. |
| 2005/0199557 A1 | 9/2005 | Johnston et al. |

OTHER PUBLICATIONS

Pestovsky, Oleg, et al., "Aqueous Ferryl(IV) Ion: Kinetics of Oxygen Atom Transfer to Substractes and Oxo Exchange with Solvent Water", American Chemical Society, Inorganic Chemistry, vol. 45, No. 2., pp. 814-820, 2006 (7 pages).

*Primary Examiner* — Sikarl Witherspoon
(74) *Attorney, Agent, or Firm* — McKee, Voohees & Sease, P.L.C.

(57) ABSTRACT

Selective oxidation of organic substrates to partially oxidized products by ozone in acetonitrile solvent, using Fe(II) catalysis.

9 Claims, No Drawings

SELECTIVE OXIDATION OF ORGANIC SUBSTRATES TO PARTIALLY OXIDIZED PRODUCTS

CROSS-REFERENCE TO RELATED APPLICATIONS

This application claims priority under 35 U.S.C. §119 to provisional application Ser. No. 61/473,316 filed Apr. 8, 2011, herein incorporated by reference in its entirety.

GRANT REFERENCE

This invention was made with government support under Contract No. DE-AC02-07CH11358 awarded by DOE. The government has certain rights in the invention.

BACKGROUND OF THE INVENTION

This invention relates to continuing discoveries and improvements over our earlier invention of U.S. Pat. No. 7,618,546 issued Nov. 17, 2009. That patent disclosed improved method and means for ozone oxidation through the addition of an iron(II) catalyst. The present invention is based upon the discovery that allows selective oxidation of organic substrates with weak C—H bonds in the presence of ozone to less than fully oxidized products, for example, oxidation to aldehydes as opposed to acids. There is a continuing desire to selectively oxidize, for example, alcohols with ozone under mild conditions in an environmentally friendly way; for example, to aldehydes without over complete over-oxidation to carboxylic acids. The invention has as its primary objective the filling of this need. The invention uses the same iron(II) catalysts in ozone oxidation, as described in our previous U.S. Pat. No. 7,618,546, which is incorporated herein by reference.

Large quantities of ozone are typically produced commercially in a modern electrical ozone generator. The passage of a high voltage, alternating electric discharge through a gas stream containing oxygen results in the breakdown of the molecular oxygen, to atomic oxygen. Some of the atoms of oxygen thus liberated can reform into ozone, while others simply recombine to again form oxygen. In order to control the electrical discharge, and maintain a "corona" or silent discharge in the gas space and avoiding as much as possible, arcing, a dielectric space or discharge gap is formed, using a dielectric material such as glass or ceramic. A ground electrode, constructed usually in 316L stainless steel (a material which has demonstrated high resistance to ozone oxidant) serves as the other boundary to the discharge space. This can be accomplished in many ways, but the most frequently employed geometry is that of the cylindrical dielectric (or Siemens Type) ozone generator. The cylindrical dielectric is more space efficient than other shaped and consequently more economical.

Ozone produced commercially for oxidation reactions is always produced as a gas, from air at concentrations between 1.5 and 2.0 percent by weight in air, or from oxygen at concentrations greater than 6% and up to 12% by weight. As ozone is highly reactive, and has a short half life, it is very difficult to store and transport. Consequently, ozone is normally generated on site for immediate use.

As described previously, the catalyst of this invention comprises iron(II). Iron is an abundant and chemically benign element that exists in multiple oxidation states for catalysis. The source of iron(II) for use as an oxidant in this invention can be many of the commercially accessible inorganic salts including, but not limited to, tetrafluoroborate, hexafluorophosphate, perchlorate, trifluoro-methane sulfonate, sulfate, and combinations thereof. The chloride and bromide salts, however, are not useful. A preferred ferrous salt for this purpose is tetrafluoroborate. The iron salts are typically purchased in solid form, then combined with acetonitrile to form a dilute solution.

The ferrous salt is used in a concentration that should be substantially less than that of the ozone. While the concentration of ozone during oxidation is generally fixed due to solubility limits of ozone, in rough terms, the concentration of ozone is preferably about 20-50 times higher than that of the iron(II) to provide an instantaneous and complete or nearly complete oxidation of the substrate. If insufficient iron(II) is used, the oxidation will still occur (as it would even without the iron catalyst), but the reaction may not be as fast or complete. If too much iron(II) is included, undesirable reactions occur with Fe(IV), resulting in an iron(III) that cannot be converted back to the iron(II) catalyst The iron catalysts of this invention, like our previous one, can be used in any applications and/or substrates for which ozone is used as an oxidant.

SUMMARY OF THE INVENTION

The present invention is directed to the discovery that organic substrates with weak C—H bonds, in the presence of ozone can selectively yield partially oxidized products if the reaction is conducted in a acetonitrile solvent, e.g., can be oxidized to aldehydes as opposed to organic acids. The reaction is conducted in the presence of iron(II).

DETAILED DESCRIPTION OF THE PREFERRED EMBODIMENTS

This discovery premised on the somewhat surprising observation that iron(II) in acetonitrile solvent catalyzes a 2-e rather than 1-e oxidation to allow selective oxidation of hydrocarbons to partially oxidized products as opposed to over oxidation to unwanted products.

Specifically, using the abundant and inexpensive iron(II) as a catalyst for oxidation with ozone in acetonitrile as solvent leads to oxidization of alcohols to aldehydes or ketones. The idea is founded on the oxidation-reduction properties of the relevant oxidation states of iron in this solvent. The results with ozone as the oxidant are highly encouraging and show that: (1) iron(II) catalyzes the reaction between ozone and alcohols, and (2) the catalytic chemistry is more selective than the uncatalyzed oxidation with $O_3$.

Our data on Fe(II) catalysis in the oxidations of alcohols and sulfoxides with ozone in acetonitrile support the involvement of a Fe(IV) intermediate, perhaps $Fe(CH_3CN)_5O^{2+}$, in analogy with the previously observed and characterized oxoiron(IV) ion, $(H_2O)_5Fe^{IV}O^{2+}$ in aqueous solutions. The apparent mechanistic shift from concurrent 1-e and 2-e pathways for the oxidation of alcohols in water to predominate (perhaps exclusive) 2-e mechanism in acetonitrile turns on catalysis. An especially interesting finding pertains to the Fe(II)-catalyzed oxidation of benzyl alcohol to benzaldehyde as dominant product, as opposed to benzoic acid. Under identical conditions but in the absence of Fe(II), the stoichiometric oxidation with ozone produces mainly benzoic acid. Similarly, methanol is oxidized to formaldehyde when iron catalyst is used. The slower reaction in the absence of the catalyst leads to more extensive oxidation to formic acid. The observed selectivity to the less oxidized product in the presence of the catalyst is highly significant in the general context of selective oxidation of hydrocarbons, a process that typically suffers from overoxidation to unwanted products.

The organic substrate that can be used in the reaction is any organic substrate that has weak C—H bonds but preferable are primary alcohols and ethers. It is believed that Fe(II) is converted to a higher oxidation state, perhaps Fe(IV) or Fe(V) that is generated in aqueous solutions as explained in our previously incorporated by reference U.S. Pat. No. 7,618,546.

The reaction is preferably run at room temperature and pressure and usually uses from about 0.1% by weight to about 1.0% by weight of the reactants of the iron(II) catalyst. The iron(II) catalyst can be selected from the group consisting of iron(II) triflate, iron(II) tetrafluoroborate and iron(II) hexafluorophosphate, for example.

The following examples are offered to illustrate but not necessarily limit the process of the present invention.

In a typical experiment, ozone was introduced into a mixture of organic substrates and Fe(II). The products, i.e. Fe(II), Fe(III) and oxidized organic materials were quantified by the methods described in our earlier patent (U.S. Pat. No. 7,618,546).

The reactions were generally run at 10 mM concentrations at which point the ratio of ozone to the catalyst was about 100:1. Ratios up to 1000:1 are very likely possible and the scale can likely be increased by at least several orders of magnitude.

Example I

Methanol to Formaldehyde 16 mM of methanol was employed, 0.4 mM of ozone was used, 10 mM of iron(II) catalyst was used. All the ozone was gone in less than 100 seconds. NMR data later revealed exclusively formaldehyde with only traces of formic acid. The reaction was conducted in acetonitrile solvent.

Example II

Benzyl Alcohol to Benzaldehyde

This reaction was conducted similarly in apparatus as the examples of U.S. Pat. No. 7,618,546, as was Example I. The reactant organic substrate was 1 mM of benzyl alcohol. Micromolar iron(II) catalyst was used; amounts of ozone 0.1 mM was used. It only took a few seconds to react. NMR showed that when it was conducted in the presence of acetonitrile over 90% of the benzyl alcohol is selectively oxidized to benzaldehyde rather than benzoic acid. From the above reactions it is expected that similar reaction kinetics will occur with other alcohols and ethers.

It can be seen from the above that the invention therefore accomplishes all of its stated objectives.

What is claimed is:

1. A method of selectively oxidizing organic substrates with weak C—H bonds, in the presence of ozone to partially oxidized products, comprising:
reacting the organic substrate and ozone in acetonitrile solvent in the presence of iron(II) catalyst.

2. The process of claim 1 wherein the organic substrate is selected from the group consisting of acetonitrile-soluble alcohols and ethers.

3. The process of claim 2 wherein the organic substrate is an alcohol.

4. The process of claim 2 wherein the organic substrate is benzyl alcohol, and the selective oxidation product benzaldehyde.

5. The process of claim 2 wherein the alcohol is methanol, and the selective oxidation product is formaldehyde.

6. The process of claim 2 wherein the organic substrate is an ether.

7. The process of claim 1 wherein the amount of catalyst is from 0.1% to 1.0% by weight of the reactants.

8. The process of claim 1 wherein the iron(II) catalyst is one which is soluble in acetonitrile.

9. The process of claim 8 wherein the iron(II) salt is selected from the group consisting of iron(II) triflate, iron II tetrafluoro borate and iron(II) hexafluorophosphate.

* * * * *